(12) United States Patent
Mitsui

(10) Patent No.: US 11,124,843 B2
(45) Date of Patent: Sep. 21, 2021

(54) METHOD AND KIT FOR DETECTING BACTERIA OF GENUS NITROBACTER

(71) Applicant: Sumitomo Chemical Company, Limited, Tokyo (JP)

(72) Inventor: Tomokazu Mitsui, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 15/563,000

(22) PCT Filed: Mar. 30, 2016

(86) PCT No.: PCT/JP2016/060560
§ 371 (c)(1),
(2) Date: Sep. 29, 2017

(87) PCT Pub. No.: WO2016/159183
PCT Pub. Date: Oct. 6, 2016

(65) Prior Publication Data
US 2018/0057858 A1    Mar. 1, 2018

(30) Foreign Application Priority Data
Apr. 3, 2015  (JP) .............................. JP2015-076951

(51) Int. Cl.
C07H 21/04    (2006.01)
C12Q 1/68     (2018.01)
C12Q 1/689    (2018.01)

(52) U.S. Cl.
CPC .................................... *C12Q 1/689* (2013.01)

(58) Field of Classification Search
None
See application file for complete search history.

(56) References Cited

U.S. PATENT DOCUMENTS 6,221,594 B1 * 4/2001 Burrell ................. C07K 14/195
                                                        435/15
2003/0157509 A1  8/2003 Mirzabekov et al.

FOREIGN PATENT DOCUMENTS

| CN | 101086023 A    | 12/2007 |
| JP | 2002538785 A   | 11/2002 |
| JP | 2012187067 A   | 10/2012 |
| JP | 2014030409 A   | 2/2014  |
| KR | 20130090296 A  | 8/2013  |

OTHER PUBLICATIONS

NEB catalog (1998/1999), pp. 121, 284. (Year: 1998).*
NEB catalog (1998/1999), pp. 121, 284. (Year: 1999).*
Rothstein et al. (1994) PNAS USA 91: 4155-4159. (Year: 1994).*
Geets (Appl Microbiol Biotechnol, vol. 75, pp. 211-221, 2007) (Year: 2007).*
Kim (Water Research, vol. 45, pp. 1267-1279, 2011) (Year: 2011).*
Montras et al. (Water Research, vol. 42, pp. 1700-1714, 2008) (Year: 2008).*
Buck et al. (BioTechniques (1999) 27(3): 528-536) (Year: 1999).*
Lowe et al. (Nucleic Acids Research (1990) 18(7): 1757-1761) (Year: 1990).*
"Nitrobacter Vulgaris Partial 16S rRNA Gene, Strain BB3," Database GenBank, May 17, 2007, downloaded from webpage,: http://www.ncbi.nlm.nih.gov/nuccore/AM286398, Download date: Jun. 6, 2016, 1 page.
"Nitrobacter Vulgaris Partial 16S rRNA Gene, Strain BB3," Database GenBank, May 1, 2007, downloaded from webpage,: http://www.ncbi.nlm.nih.gov/nuccore/AM286398, Download date: Jun. 6, 2016, 1 page.
"*Nitrobacter* sp. lo acid partial 16S rRNA gene, strain lo acid," Database GenBank, Jul. 31, 2007, downloaded from webpage,: http://www.ncbi.nlm.nih.gov/nuccore/AM292298, Download date: Jun. 6, 2016, 1 page.
Graham et al.,, "Experimental demonstration of chaotic instability in biological nitrification," The International Society for Microbial Ecology Journal, vol. 1, pp. 385-393 (2007).
Geets et al., "Real-time PCR assay for the simultaneous quantification of nitrifying and denitrifying bacteria in activated sludge," Appl. Microbiol Biotechnology, vol. 75, pp. 211-221 (2007).
Int'l Search Report dated Jun. 14, 2016 in Int'l Application No. PCT/JP2016/060560.
Int'l Preliminary Report on Patentability dated Oct. 12, 2017 in Int'l Application No. PCT/JP2016/060560.
Office Action dated Nov. 20, 2020 in CN Application No. 201680019328.5.
Coskuner et al., "In situ characterization of nitrifiers in an activated sludge plant: detection of *Nitrobacter* spp.," Journal of Applied Microbiology, vol. 93, pp. 431-437 (2002).
GenBank: AM286395.1, "*Nitrobacter* sp. lo acid partial 16S rRNA gene, strain lo acid," 2 pages (2007).
Office Action dated Apr. 29, 2020 in TW Application No. 105110518.
Rezaee, et al., "Molecular identification of nitrifying bacteria in activated sludge", J Mater Environ, Sci 4 (5), pp. 601-604, 2013.
Cham, Characterization of the nitrobacter-specific NIT3 and Nb1000 probes and their use in the detection of *Nitrobacter* species in a lab scale completely stirred tank reactor system, Journal of Experimental Microbiology and Immunology, vol. 4, pp. 7-14, 2003.

(Continued)

*Primary Examiner* — Jeanine A Goldberg
(74) *Attorney, Agent, or Firm* — Panitch Schwarze Belisario & Nadel LLP

(57) ABSTRACT

Provided is a method for detecting a bacterium of the genus *Nitrobacter*, comprising: a first step of amplifying a nucleotide using a test DNA as a template and primers capable of amplifying a nucleotide sequence of consecutive 110 nucleotides or more and 157 nucleotides or less in the nucleotide sequence set forth in SEQ ID NO: 1 to obtain an amplified product; and a second step of detecting the amplified product.

2 Claims, No Drawings
Specification includes a Sequence Listing.

(56) References Cited

OTHER PUBLICATIONS

Harms, Gerda, et al., "Real-time PCR quantification of nitrifying bacteria in a municipal wastewater treatment plant", Environmental Science & Technology, vol. 37 No. 2, pp. 343-351, 2003.

Ramdhani, "Detection and Quantification of Nitrifying Bacteria from South African Biological Nutrient Removal Plants", 194 pages, Oct. 2012.

Degrange et al., "Detection and counting of Nitrobacter populations in soil by PCR", Applied and Environmental Microbiology, vol. 61, No. 6, pp. 2093-2098, 1995.

* cited by examiner

SEQUENCE LISTING

<160> NUMBER OF SEQ ID NOS: 22

<210> SEQ ID NO 1
<211> LENGTH: 157
<212> TYPE: DNA
<213> ORGANISM: Nitrobacter sp.

<400> SEQUENCE: 1

```
ccagcccttg acatgtccat gaccggtcgc agagatgtga ccttctcttc ggagcatgga      60
gcacaggtgc tgcatggctg tcgtcagctc gtgtcgtgag atgttgggtt aagtcccgca     120
acgagcgcaa ccccgtcct tagttgctac catttag                              157
```

```
<210> SEQ ID NO 2
<211> LENGTH: 40
<212> TYPE: DNA
<213> ORGANISM: Nitrobacter sp.

<400> SEQUENCE: 2
ccagcccttg acatgtccat gaccggtcgc agagatgtga                    40

<210> SEQ ID NO 3
<211> LENGTH: 28
<212> TYPE: DNA
<213> ORGANISM: Nitrobacter sp.

<400> SEQUENCE: 3 accccgtcc ttagttgcta ccatttag                                  28

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
ccagcccttg acatgtccat                                          20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
cccttgacat gtccatgacc                                          20

<210> SEQ ID NO 6
<211> LENGTH: 18
<212> TYPE: DNA
<213> ORGANISM: Artificial Sequence
<220> FEATURE:
<223> OTHER INFORMATION: synthetic

<400> SEQUENCE: 6
gtccatgacc ggtcgcag                                            18

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
atgaccggtc gcagagat                                            18

<210> SEQ ID NO 8
<211> LENGTH: 18
<212> TYPE: DNA
<213> ORGANISM: Artificial Sequence
<220> FEATURE:
<223> OTHER INFORMATION: synthetic

<400> SEQUENCE: 8
ccggtcgcag agatgtga                                            18
```

<210> SEQ ID NO 9
<211> LENGTH: 22
<212> TYPE: DNA
<213> ORGANISM: Artificial Sequence
<220> FEATURE:
<223> OTHER INFORMATION: synthetic

<400> SEQUENCE: 9
ctaaatggta gcaactaagg ac                                              22

<210> SEQ ID NO 10
<211> LENGTH: 22
<212> TYPE: DNA
<213> ORGANISM: Artificial Sequence
<220> FEATURE:
<223> OTHER INFORMATION: synthetic

<400> SEQUENCE: 10
ggtagcaact aaggacgggg gt                                              22

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cctgtgctcc atgctccg                                                   18

<210> SEQ ID NO 12
<211> LENGTH: 21
<212> TYPE: DNA
<213> ORGANISM: Artificial Sequence
<220> FEATURE:
<223> OTHER INFORMATION: synthetic

<400> SEQUENCE: 12
ttagtgggtt tactcactag t                                               21

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
tgggtttact cactagtggc g                                               21

<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
tttactcact agtggcgcag c                                               21

<210> SEQ ID NO 15
<211> LENGTH: 21
<212> TYPE: DNA
<213> ORGANISM: Artificial Sequence
<220> FEATURE:

```
<223> OTHER INFORMATION: synthetic

<400> SEQUENCE: 15
ctcactagtg gcgcagctaa c                                              21

<210> SEQ ID NO 16
<211> LENGTH: 22
<212> TYPE: DNA
<213> ORGANISM: Artificial Sequence
<220> FEATURE:
<223> OTHER INFORMATION: synthetic

<400> SEQUENCE: 16
caactaagga cggggttgc gc                                              22

<210> SEQ ID NO 17
<211> LENGTH: 18
<212> TYPE: DNA
<213> ORGANISM: Artificial Sequence
<220> FEATURE:
<223> OTHER INFORMATION: synthetic

<400> SEQUENCE: 17
ctccatgctc cgaagaga                                                  18

<210> SEQ ID NO 18
<211> LENGTH: 1411
<212> TYPE: DNA
<213> ORGANISM: Nitrobacter sp.

<400> SEQUENCE: 18
agcgaacgct ggcggcaggc ttaacacatg caagtcgaac gggcgtagca atacgtcagt     60
ggcagacggg tgagtaacgc gtgggaacgt acctttggt tcggaacaac acagggaaac    120
ttgtgctaat accggataag cccttacggg gaaagattta tcgccgaaag atcggcccgc    180
gtctgattag cttgttggtg aggtaatggc tcaccaaggc gacgatcagt agctggtctg    240
agaggatgat cagccacatt gggactgaga cacggcccaa actcctacgg gaggcagcag    300
tggggaatat tggacaatgg gcgcaagcct gatccagcca tgccgcgtga gtgatgaagg    360
ccctagggtt gtaaagctct tttgtgcggg aagataatga cggtaccgca gaataagcc     420 ccggctaact tcgtgccagc agccgcggta atacgaaggg gctagcgtt gctcggaatt     480 actgggcgta agggtgcgt aggcgggtct ttaagtcaga ggtgaaatcc tggagctcaa    540
ctccagaact gcctttgata ctgaggatct tgagttcggg agaggtgagt ggaactgcga    600
gtgtagaggt gaaattcgta gatattcgca agaacaccag tggcgaaggc ggctcactgg    660
cccgatactg acgctgaggc acgaaagcgt ggggagcaaa caggattaga taccctggta    720
gtccacgccg taaacgatga atgccagccg ttagtgggtt tactcactag tggcgcagct    780
aacgctttaa gcattccgcc tggggagtac ggtcgcaaga ttaaaactca aggaattga    840 cgggggcccg cacaagcggt ggagcatgtg gtttaattcg acgcaacgcg cagaaccta    900 ccagcccttg acatgtccat gaccggtcgc agagatgtga ccttctcttc ggagcatgga    960
gcacaggtgc tgcatggctg tcgtcagctc gtgtcgtgag atgttgggtt aagtcccgca   1020
acgagcgcaa ccccgtcct tagttgctac catttagttg agcactctaa ggagactgcc   1080
ggtgataagc cgcgaggaag gtgggatga cgtcaagtcc tcatggccct tacgggctgg   1140
gctacacacg tgctacaatg gcggtgacaa tgggaagcaa aggggcaacc cctagcaaat   1200
ctcaaaaaac cgtctcagtt cggattgggc tctgcaaccc gagcccatga agttggaatc   1260
```

```
gctagtaatc gtggatcagc atgccacggt gaatacgttc ccgggccttg tacacaccgc    1320
ccgtcacacc atgggagttg gttttacctg aaggcggtgc gctaacccgc aagggaggca    1380
gccgaccacg gtagggtcag cgactggggt g                                   1411

<210> SEQ ID NO 19
<211> LENGTH: 18
<212> TYPE: DNA
<213> ORGANISM: Artificial Sequence
<220> FEATURE:
<223> OTHER INFORMATION: synthetic

<400> SEQUENCE: 19
tttttTgaga tttgctag                                                      18

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
ctaaaactca aaggaattga                                                    20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
agrgtttgat cmtggctcag                                                    20

<210> SEQ ID NO 22
<211> LENGTH: 19
<212> TYPE: DNA
<213> ORGANISM: Artificial Sequence
<220> FEATURE:
<223> OTHER INFORMATION: synthetic

<400> SEQUENCE: 22
ggytaccttg ttacgactt                                                     19
```

METHOD AND KIT FOR DETECTING BACTERIA OF GENUS NITROBACTER

CROSS-REFERENCE TO RELATED APPLICATION

This application is a Section 371 of International Application No. PCT/JP2016/060560, filed Mar. 30, 2016, which was published in the Japanese language on Jun. 10, 2016 under International Publication No. WO 2016/159183 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688101_0053", creation date of Sep. 27, 2017, and having a size of 6.1 KB. The sequence listing submitted via EFS-Web is part of the specification and is herein incorporated by reference in its entirety.

TECHNICAL FIELD

The present invention relates to a method and a kit for detecting a bacterium of the genus *Nitrobacter*.

BACKGROUND ART

As nitrifying bacteria, ammonia-oxidizing bacteria (nitrite bacteria), which oxidize ammonia to nitrite, and nitrite-oxidizing bacteria (nitrate bacteria), which oxidize nitrite to nitrate, are known. These nitrifying bacteria are responsible for nitrogen cycle reactions in the natural world. Meanwhile, in the industry, the nitrifying bacteria play an important role, for example, in the nitrogen removal in the biological treatment process of drainage, represented by the activated sludge process and are involved in the prevention of eutrophication of natural waters due to the outflow of nitrogenous salts.

Activated sludge used in drainage treatment includes various kinds of microorganisms, among which bacteria of the genus *Nitrobacter* are a kind of nitrite-oxidizing bacteria, which play an important role in the nitrogen removal. In the nitrogen removal, it is desired to monitor and regulate the amount of bacteria of the genus *Nitrobacter* in activated sludge according to the amount of nitrogen in drainage and the treatment speed required for the drainage treatment. To that end, it is a problem to rapidly detect and quantify only bacteria of the genus *Nitrobacter* in the activated sludge in which a plurality of microorganisms is present.

Non Patent Literatures 1 and 2 describe real-time PCR with certain primers and a fluorescently labeled probe for detecting bacteria of the genus *Nitrobacter*.

CITATION LIST

Non Patent Literature

Non Patent Literature 1: David W Graham et. al., The ISME Journal vol. 1 (2007), p. 385-393
Non Patent Literature 2: Joke Geeks et. al., Appl Microbiol Biotechnol. vol. 75 (2007), p. 211-221

SUMMARY OF INVENTION

Technical Problem

However, when the present inventors tried the detection of bacteria of the genus *Nitrobacter* in activated sludge using the primers and fluorescently labeled probes described in Non-Patent Literatures 1 and 2, problems occurred such as those that bacteria other than the bacteria of the genus *Nitrobacter* were detected or that it was not possible to detect some of the bacteria of the genus *Nitrobacter*. If such a problem occurs, then the quantifiability of the bacteria of the genus *Nitrobacter* is also affected and it becomes difficult to control the reactions for removing nitrogen in drainage.

In view of the aforementioned circumstances, an object of the present invention is to provide a method for detecting a bacterium of the genus *Nitrobacter*, the method being capable of specifically detecting and quantifying the bacterium of the genus *Nitrobacter* even in systems in which a plurality of kinds of microorganisms is present and a kit to be used therefor.

Solution to Problem

The present inventors cloned a nucleotide sequence (SEQ ID NO: 18) of the 16S rRNA gene of a bacterium of the genus *Nitrobacter* present in activated sludge and newly found that particular regions are useful for the specific detection and quantification of the bacteria of the genus *Nitrobacter* in systems in which a plurality of kinds of microorganisms is present, thereby completing the present invention.

Accordingly, the present invention relates to, for example, the following [1] to [6]:

[1] A method for detecting a bacterium in the genus *Nitrobacter*, comprising: a first step of amplifying a nucleotide using a test DNA as a template and primers capable of amplifying a nucleotide sequence of consecutive 110 nucleotides or more and 157 nucleotides or less in the nucleotide sequence set forth in SEQ ID NO: 1 to obtain an amplified product; and a second step of detecting the amplified product.

[2] The method according to [1], wherein the primers used in the first step are a first primer comprising a nucleotide sequence of 18 nucleotides or more that hybridizes with a nucleotide comprising a nucleotide sequence complementary to the nucleotide sequence set forth in SEQ ID NO: 2 under stringent conditions and a second primer comprising a nucleotide sequence of 18 nucleotides or more that hybridizes with a nucleotide comprising the nucleotide sequence set forth in SEQ ID NO: 3 under stringent conditions.

[3] The method according to [2], wherein the first primer comprises one nucleotide sequence selected from nucleotide sequences set forth in SEQ ID NOs: 4 to 8 and the second primer comprises one nucleotide sequence selected from nucleotide sequences set forth in SEQ ID NO: 9 or 10.

[4] The method according to any one of [1] to [3], wherein the second step comprises detecting the amplified product using a probe comprising the nucleotide sequence set forth in SEQ ID NO: 11.

[5] A kit to be used in detection of a bacterium in the genus *Nitrobacter*, comprising: a first primer comprising a nucleotide sequence of 18 nucleotides or more that hybridizes with a nucleotide comprising a nucleotide sequence complementary to the nucleotide sequence set forth in SEQ ID NO: 2 under stringent conditions and a second primer comprising a nucleotide sequence of 18 nucleotides or more that hybridizes with the nucleotide sequence set forth in SEQ ID NO: 3 under stringent conditions; and a probe comprising the nucleotide sequence set forth in SEQ ID NO: 11.

[6] The kit according to [5], wherein the first primer comprises one nucleotide sequence selected from nucleotide sequences set forth in SEQ ID NOs: 4 to 8 and the second primer comprises one nucleotide sequence selected from nucleotide sequences set forth in SEQ ID NO: 9 or 10.

Advantageous Effects of Invention

According to the present invention, it is possible to provide a method for detecting a bacterium of the genus *Nitrobacter*, the method being capable of specifically detecting and quantifying the bacterium of the genus *Nitrobacter* even in systems in which a plurality of kinds of microorganisms is present and a kit to be used therefor. By virtue of this, for example, the reactions for removing nitrogen in drainage can be controlled based on the amount of the bacteria of the genus *Nitrobacter* detected in activated sludge in drainage treatment.

DESCRIPTION OF EMBODIMENTS

A mode for carrying out the present invention (hereinafter, referred to as the "the present embodiment") is described in detail below. The present invention is not limited to the following embodiment.

<Method for Detecting Bacteria of Genus *Nitrobacter*>

A method for detecting a bacterium in the genus *Nitrobacter* of the present embodiment comprises a first step of amplifying a nucleotide using a test DNA as a template and primers capable of amplifying a nucleotide sequence of consecutive 110 nucleotides or more and 157 nucleotides or less in the nucleotide sequence set forth in SEQ ID NO: 1 to obtain an amplified product; and a second step of detecting the amplified product.

Examples of the test DNA according to the present embodiment include a plasmid, cDNA, genomic DNA, and DNA prepared from activated sludge. The test DNA may comprise DNA derived from a plurality of kinds of microorganisms. As a method for preparing the test DNA, a method well known to those skilled in the art may be used. As the test DNA, DNA prepared from activated sludge is preferred from the point of view of controlling reactions for removing nitrogen in drainage. As a method for preparing DNA from activated sludge, for example, commercially available DNA extraction kits may be used.

[First Step]

SEQ ID NO: 1 sets forth a nucleotide sequence of the positions 901 to 1057 of SEQ ID NO: 18. SEQ ID NO: 18 sets forth a nucleotide sequence of the 16S rRNA gene of a bacterium of the genus *Nitrobacter*. In the 16S rRNA gene, there are preserved regions containing common sequences between species on the gene and 9 variable regions (V1 to V9) containing sequences that vary depending on the species, the genus, or the like. In SEQ ID NO: 18, a nucleotide sequence of the positions 747 to 774 is the V5 region, a nucleotide sequence of the positions 920 to 966 is the V6 region, and a nucleotide sequence of the positions 1038 to 1074 is the V7 region.

The nucleotide sequence set forth in SEQ ID NO: 1 is a region containing the V6 and V7 regions of the 16S rRNA gene. In the first step according to the present embodiment, the amplified product is prepared by amplifying a nucleotide using primers capable of amplifying a nucleotide sequence of consecutive 110 nucleotides or more and 157 nucleotides or less in the nucleotide sequence set forth in SEQ ID NO: 1. The amplified product may be prepared by amplifying a nucleotide using primers capable of amplifying a nucleotide sequence of consecutive 120 nucleotides or more and 157 nucleotides or less or using primers capable of amplifying a nucleotide sequence of consecutive 125 nucleotides or more and 157 nucleotides or less. The amplified product may be a nucleotide sequence having 1 to 2 nucleotides different from the correspondent region in the nucleotide sequence set forth in SEQ ID NO: 1 or a nucleotide sequence having the same nucleotides as long as it is prepared by the amplification using such primers. By using the aforementioned amplified product, the bacteria of the genus *Nitrobacter* can be specifically detected in the subsequent second step.

The method for amplifying the nucleotide to obtain an amplified product in the first step is not particularly limited, but a method well-known to those skilled in the art may be used. Examples of such a method include polymerase chain reaction (PCR), real-time PCR, and LAMP. Among these methods, real-time PCR is preferred since, at the same time as the amplification, the detection in the second step may be conducted and the amplified product may be quantified.

The primer used to obtain the amplified product may be designed so as to be capable of amplifying a region containing the part from the V6 region to the V7 region (the nucleotide sequence region of the positions 901 to 1057 of SEQ ID NO: 18) of the 16S rRNA gene of the bacteria of the genus *Nitrobacter*. The primers are a first primer (forward primer) that hybridizes with the antisense strand of the DNA encoding 16S rRNA under stringent conditions and a second primer (reverse primer) that hybridizes with the sense strand under stringent conditions.

As the first primer, a primer that hybridizes with a nucleotide comprising the nucleotide sequence complementary to the nucleotide sequence set forth in SEQ ID NO: 2 under stringent conditions is preferable. The length of the primer is preferably 18 nucleotides or more from the point of view of obtaining more sufficient specificity. The upper limit of the length of the primer is preferably 28 nucleotides or less, more preferably 27 nucleotides or less, and further preferably 25 nucleotides or less from the point of view of increasing annealing efficiency. Specific examples of the first primer include a primer comprising a nucleotide sequence selected from the nucleotide sequences set forth in SEQ ID NOs: 4 to 8.

Examples of the primer comprising a nucleotide sequence of 18 nucleotides or more that hybridizes with a nucleotide comprising the nucleotide sequence complementary to the nucleotide sequence set forth in SEQ ID NO: 2 under stringent conditions include a primer comprising a nucleotide sequence having 2 nucleotides different from a nucleotide sequence of consecutive 18 nucleotides or more in the nucleotide sequence set forth in SEQ ID NO: 2, preferably a primer comprising a nucleotide sequence having 1 nucleotide different from a nucleotide sequence of consecutive 18 nucleotides or more in the nucleotide sequence set forth in SEQ ID NO: 2, and more preferably a primer comprising a nucleotide sequence of consecutive 18 nucleotides or more in the nucleotide sequence set forth in SEQ ID NO: 2.

As the second primer, a primer that hybridizes with a nucleotide comprising the nucleotide sequence set forth in SEQ ID NO: 3 under stringent conditions is preferable. The length of the primer is preferably 18 nucleotides or more, more preferably 19 nucleotides or more, and further preferably 20 nucleotides or more from the point of view of obtaining more sufficient specificity. The upper limit of the length of the primer is preferably 28 nucleotides or less, more preferably 27 nucleotides or less, and further preferably 25 nucleotides or less from the point of view of increasing annealing efficiency. Specific examples of the second primer include a primer comprising a nucleotide sequence selected set forth in SEQ ID NO: 9 or 10.

Examples of the primer comprising a nucleotide sequence of 18 nucleotides or more that hybridizes with a nucleotide comprising the nucleotide sequence set forth in SEQ ID NO: 3 under stringent conditions include a primer comprising a nucleotide sequence having 2 nucleotides different from a nucleotide sequence of consecutive 18 nucleotides or more in the nucleotide sequence complementary to the nucleotide sequence set forth in SEQ ID NO: 3, preferably a primer comprising a nucleotide sequence having 1 nucleotide different from a nucleotide sequence of consecutive 18 nucleotides or more in the nucleotide sequence complementary to the nucleotide sequence set forth in SEQ ID NO: 3, and more preferably a primer comprising a nucleotide sequence of consecutive 18 nucleotides or more in the nucleotide sequence complementary to the nucleotide sequence set forth in SEQ ID NO: 3.

As used herein, "stringent conditions" means conditions under which complementary strands of nucleotide strands having a homology with a target sequence preferentially hybridize to the target sequence and complementary strands of nucleotide strands that do not have such a homology do not substantially hybridize. Stringent conditions are sequence-dependent and vary in a variety of situations. Longer sequences specifically hybridize at higher temperatures. In general, stringent conditions are selected so that the temperature is about 5° C. lower than the thermal melting temperature (Tm) of the particular sequence at the prescribed ionic strength and pH. Tm is a temperature at which 50% of nucleotides complementary to the target sequence hybridize to the target sequence in equilibrium under the prescribed ionic strength, pH, and DNA concentration.

Examples of the "primer comprising a nucleotide sequence that hybridizes under stringent conditions" include primers that hybridize a nucleotide of interest at high ion concentrations [for example, 6×SSC (900 mM sodium chloride, 90 mM sodium citrate) or the like is used.] at a temperature condition of 65° C. to form a DNA-DNA hybrid and this hybrid is maintained even after washing for 30 minutes at low ion concentrations [for example, 0.1×SSC (15 mM sodium chloride, 1.5 mM sodium citrate) or the like is used.] at a temperature condition of 65° C.

[Second Step]

A method for detecting the amplified product in the second step is not particularly limited, but a method well-known to those skilled in the art may be used. Examples of the method for detecting the amplified product include agarose gel electrophoresis, real-time PCR, sequence analysis, and Southern blotting. Among these methods, detection methods using a probe are preferred from the point of view of superior specificity. Examples of the detection methods using a probe include real-time PCR or Southern blotting and, among them, real-time PCR is preferred from the point of view of being capable of conducting the amplification in the first step at the same time and specific detection and superior quantifiability.

As a probe used in the detection, oligonucleotides that hybridize with sense or antisense strands of the amplified product obtained in the first step under stringent conditions are preferable. The length of the probe is preferably 15 nucleotides or more and 30 nucleotides or less, more preferably 15 nucleotides or more and 25 nucleotides or less, and further preferably 15 nucleotides or more and 20 nucleotides or less from the point of view of specifically detecting the amplified product. Specific examples of the probe include probes comprising the nucleotide sequence set forth in SEQ ID NO: 11.

If the aforementioned probe is used in real-time PCR, then the probe is modified with a fluorescent substance at the 5' end and a quencher, which inhibits the fluorescence that the fluorescent substance emits, at the 3' end, respectively. Examples of the fluorescent substance include FAM, TET, HEX, TAMRA, and Cyanine5. Examples of the quencher include TAMRA, BHQ1, BHQ2, and BHQ3. The fluorescent substance and quencher used for the modification of the probe may be selected as appropriate according to the excitation wavelength and the measurement wavelength of the real-time PCR apparatus to be used.

The real-time PCR apparatus is not particularly limited, as long as it includes a thermal cycler that can amplify DNA by PCR and a spectrofluorometer for detecting the amplified product. Examples of the real-time PCR apparatus include StepOnePlus (manufactured by Applied Biosystems).

The amplified sample detected in the second step may be quantified. Therefore, the detection method of the present embodiment may involve not only detecting the bacteria of the genus *Nitrobacter* in the test DNA, but also quantifying the amount of the bacteria of the genus *Nitrobacter* included in the test DNA. For example, if real-time PCR is used for the detection of the amplified product in the second step, then the amount of the test DNA may be quantified from a standard curve obtained using standard samples. The standard curve may be made based on Ct values indicating the number of cycles with which the amplified product reaches a certain value and the initial amounts of the template.

In the detection method of the present embodiment, if an amplified product is obtained from the test DNA in the first step and it was possible to detect the amplified product in the second step, it can be determined that the DNA derived from the bacteria of the genus *Nitrobacter* is contained in the test DNA.

<Kit of Bacteria of Genus *Nitrobacter*>

The kit used for the detection of the bacteria of the genus *Nitrobacter* of the present embodiment comprises a first primer comprising a nucleotide sequence of 18 nucleotides or more that hybridizes with the nucleotide sequence complementary to the nucleotide sequence set forth in SEQ ID NO: 2 under stringent conditions and a second primer comprising a nucleotide sequence of 18 nucleotides or more that hybridizes with the nucleotide sequence set forth in SEQ ID NO: 3 under stringent conditions; and a probe comprising the nucleotide sequence set forth in SEQ ID NO: 11.

As the first primer, the second primer, and the probe, those similar to a primer or probe used in the aforementioned detection method may be used.

To the kit of the present embodiment, other reagents or the like may be attached as needed besides the first primer, the second primer, and the probe comprising the nucleotide sequence set forth in SEQ ID NO: 11. Examples of the other reagents include a DNA polymerase, a deoxyribonucleotide mixture (dNTP Mix), buffer solutions, sterilized water, and DNA for control.

If buffer solutions are attached to the kit of the present embodiment, examples of the buffer solutions include buffer solutions that are used in common PCR.

EXAMPLES

Example 1: Selection of Primer and Probe (Materials)

In order to amplify a 16S rRNA gene derived from a bacterium of the genus *Nitrobacter*, primers and probes were designed. Primers and a probe for amplifying the V6-V7 regions of the 16S rRNA and primers and probes for amplifying the V5-V7 regions are illustrated in Table 1 and Table 2, respectively. Moreover, as primers for amplifying the 16S rRNA gene derived from bacteria of the genus *Nitrobacter*, primers having the nucleotide sequences set forth in SEQ ID NO: 19 and SEQ ID NO: 20 described in Non Patent Literature 2 were also used. As template DNA, a plasmid in which a nucleotide sequence (SEQ ID NO: 18) of the 16S rRNA gene derived from a bacterium of the genus *Nitrobacter* was introduced was used. The template DNA was obtained by preparing an amplified product by PCR using primers having the nucleotide sequences set forth in SEQ ID NOs: 21 and 22 and DNA extracted from the bacterium of the genus *Nitrobacter* as a template and then introducing the amplified product into a plasmid. The PCR reaction was conducted: (1) at 94° C., for 2 minutes, (2) at 98° C., for 10 seconds, (3) at 60° C. to 40° C., for 30 seconds, and (4) at 68° C., for 1.5 minutes and the steps of (2) to (4) were repeated for 35 cycles.

TABLE 1

| Kind | Region | SEQ ID NO: | Name |
|---|---|---|---|
| Forward primers | V6 | 4 | FP1 |
| | | 5 | FP2 |
| | | 6 | FP3 |
| | | 7 | FP4 |
| | | 8 | FP5 |
| Reverse primers | V7 | 9 | RP1 |
| | | 10 | RP2 |
| Fluorescently labeled probe (5' end: 6-FAM modified 3' end: TAMRA) | Between V6-V7 | 11 | Probe 1 |

TABLE 2

| Kind | Region | SEQ ID NO: | Name |
|---|---|---|---|
| Forward primers | V5 | 12 | FP6 |
| | | 13 | FP7 |
| | | 14 | FP8 |
| | | 15 | FP9 |
| Reverse primers | V7 | 9 | RP1 |
| | | 10 | RP2 |
| | | 16 | RP3 |
| Fluorescently labeled probe (5' end: 6-FAM modified 3' end: TAMRA) | Between V6-V7 | 11 | Probe 1 |
| | | 17 | Probe 2 |

(Method)

Using the primers and probes set forth in Tables 1 and 2, the 16S rRNA gene of the bacterium of the genus *Nitrobacter* was amplified with a real-time PCR apparatus (StepOnePlus, manufactured by Applied Biosystems).

10 μL of 2× TaqMan fast Advanced Master Mix (manufactured by Life technologies), 0.36 μL of a forward primer (50 pmol/μL), 0.36 L of a reverse primer (50 pmol/μL), 0.50 μL of a probe, 6.78 μL of sterilized water, and 2.00 μL of template DNA were added to a microtube and mixed. The microtube was placed in the real-time PCR apparatus and the amplification reaction was conducted. The reaction was conducted (1) at 95° C., for 20 seconds, (2) at 95° C., for 1 second, and (3) at 60° C., for 20 seconds and the steps (2) and (3) were repeated for 50 cycles. The progress of the reaction was confirmed in real time by irradiation with excitation light at 492 nm and measurement of fluorescence (515 nm) of the fluorescent substance 6-FAM.

(Result)

The combinations of primers and a probe with which it was possible to amplify the 16S rRNA gene derived from a bacterium of the genus *Nitrobacter* are illustrated in Tables 3 and 4. 10 sets of primers and a probe designed within the V6-V7 regions and 11 sets of primers and a probe designed within the V5-V7 regions were those with which it was possible to detect the plasmid in which the nucleotide sequence (SEQ ID NO: 18) of the 16S rRNA gene derived from a bacterium of the genus *Nitrobacter* was introduced and it was possible to detect 1 pg/μL to 0.001 pg/μL of the plasmid. On the other hand, it was not possible to detect the plasmid in which the 16S rRNA gene having the nucleotide sequence set forth in SEQ ID NO: 18 was introduced with the combination of primers having the nucleotide sequences set forth in SEQ ID NO: 19 and SEQ ID NO: 20 and Probe 1.

TABLE 3

| V6-V7 region | Combinations | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Forward primer | FP1 | FP2 | FP3 | FP4 | FP5 | FP1 | FP2 | FP3 | FP4 | FP5 |
| Reverse primer | RP1 | RP1 | RP1 | RP1 | RP1 | RP2 | RP2 | RP2 | RP2 | RP2 |
| Probe | Probe 1 | Probe 1 | Probe 1 | Probe 1 | Probe 1 | Probe 1 | Probe 1 | Probe 1 | Probe 1 | Probe 1 |

TABLE 4

| V5-V7 region | Combinations | | | | | | | | | | |
|---|---|---|---|---|---|---|---|---|---|---|---|
| | 2-1 | 2-2 | 2-3 | 2-4 | 2-5 | 2-6 | 2-7 | 2-8 | 2-9 | 2-10 | 2-11 |
| Forward primer | FP7 | FP8 | FP9 | FP6 | FP7 | FP8 | FP9 | FP6 | FP7 | FP9 | FP6 |
| Reverse primer | RP1 | RP1 | RP1 | RP2 | RP2 | RP2 | RP2 | RP2 | RP3 | RP3 | RP2 |

TABLE 4-continued

| V5-V7 region | Combinations | | | | | | | | | | |
|---|---|---|---|---|---|---|---|---|---|---|---|
| | 2-1 | 2-2 | 2-3 | 2-4 | 2-5 | 2-6 | 2-7 | 2-8 | 2-9 | 2-10 | 2-11 |
| Probe | Probe 1 | Probe 1 | Probe 1 | Probe 1 | Probe 1 | Probe 1 | Probe 1 | Probe 1 | Probe 1 | Probe 1 | Probe 2 |

Example 2: Specificity Test with 1 Kind of Plasmid (Materials)

Combination 1-2, 1-4, 1-5, 1-7, 1-9, 1-10, or 2-5 of primers and a probe

Plasmids in which the 16S rRNA genes derived from various bacteria were introduced (derived from the bacteria set forth in Table 5).

(Method)

Real-time PCR was conducted by a method similar to that in Example 1 except that the aforementioned primers and probe were used and that any one of the aforementioned plasmids was used as template DNA.

(Result)

Table 5 illustrates the names of the bacteria genera from which the 16S rRNA genes introduced into the plasmid used for the test are derived and the results of detection of these plasmids. Using the combinations (1-2, 1-4, 1-5, 1-7, 1-9, 1-10) of primers and a probe designed within the V6-V7 regions and the combination (2-5) of primers and a probe designed within the V5-V7 regions, the plasmids in which the 16S rRNA gene derived from a bacterium other than the bacteria of the genus *Nitrobacter* was introduced were below the detection limit (0.001 pg/μL). Moreover, these sets of primers and a probe exhibited no detectability for bacteria of the genus *Bradyrhizobium*, which is close species of the bacteria of the genus *Nitrobacter*. Thus, it was demonstrated that it is possible to specifically detect the bacteria of the genus *Nitrobacter* with these primers and probe.

TABLE 5

| Name of bacterial genus | Theoretical value of plasmid (pg/μL) | Detection result of plasmid Combinations of primer and probe | | | | | | |
|---|---|---|---|---|---|---|---|---|
| | | 1-2 | 1-4 | 1-5 | 1-7 | 1-9 | 1-10 | 2-5 |
| *Novosphingobium* | 1 | Below detection limit | Below detection limit | Below detection limit | Below detection limit | Below detection limit | Below detection limit | Below detection limit |
| *Xanthobacter* | 1 | Below detection limit | Below detection limit | Below detection limit | Below detection limit | Below detection limit | Below detection limit | Below detection limit |
| *Sediminibacterium* | 1 | Below detection limit | Below detection limit | Below detection limit | Below detection limit | Below detection limit | Below detection limit | Below detection limit |
| *Rhodococcus* | 1 | Below detection limit | Below detection limit | Below detection limit | Below detection limit | Below detection limit | Below detection limit | Below detection limit |
| *Methyloversatilis* | 1 | Below detection limit | Below detection limit | Below detection limit | Below detection limit | Below detection limit | Below detection limit | Below detection limit |
| *Methylibium* | 1 | Below detection limit | Below detection limit | Below detection limit | Below detection limit | Below detection limit | Below detection limit | Below detection limit |
| *Sphingomonas* | 1 | Below detection limit | Below detection limit | Below detection limit | Below detection limit | Below detection limit | Below detection limit | Below detection limit |
| *Haliscomenobacter* | 1 | Below detection limit | Below detection limit | Below detection limit | Below detection limit | Below detection limit | Below detection limit | Below detection limit |
| *Nitrosomonas* | 1 | Below detection limit | Below detection limit | Below detection limit | Below detection limit | Below detection limit | Below detection limit | Below detection limit |
| *Thermomonas* | 1 | Below detection limit | Below detection limit | Below detection limit | Below detection limit | Below detection limit | Below detection limit | Below detection limit |
| *Bradyrhizobium* | 1 | Below detection limit | Below detection limit | Below detection limit | Below detection limit | Below detection limit | Below detection limit | Below detection limit |
| *Rhodoplanes* | 1 | Below detection limit | Below detection limit | Below detection limit | Below detection limit | Below detection limit | Below detection limit | Below detection limit |
| *Nitrobacter* | 1 | Detectable | Detectable | Detectable | Detectable | Detectable | Detectable | Detectable |
| | 0.1 | Detectable | Detectable | Detectable | Detectable | Detectable | Detectable | Detectable |
| | 0.01 | Detectable | Detectable | Detectable | Detectable | Detectable | Detectable | Detectable |
| | 0.001 | Detectable | Detectable | Detectable | Detectable | Detectable | Detectable | Detectable |

Example 3: Specificity Test and Quantifiability Test with Mixed Plasmids of Plurality of Kinds (Materials)

Combination 1-2, 1-4, 1-5, 1-7, 1-9, 1-10, 2-5 of primers and a probe.

Plasmids in which the nucleotide sequence (SEQ ID NO: 18) of the 16S rRNA gene derived from a bacterium of the genus *Nitrobacter* is introduced.

Plasmids in which the 16S rRNA genes derived from various bacteria were introduced (derived from the bacteria set forth in Table 5).

(Method)

To a mixture (the final concentrations of the various kinds of plasmids were each 1 pg/µL) in which the plasmids in which the 16S rRNA genes derived from 12 kinds of bacteria other than the bacteria of the genus *Nitrobacter* among the bacteria set forth in Table 5 were introduced were mixed, a plasmid in which the 16S rRNA gene derived from a bacterium of the genus *Nitrobacter* was introduced was admixed at a final concentration of 1 pg/µL, 0.1 pg/µL, 0.01 pg/µL, or 0.001 pg/µL to prepare a plasmid mixture. Real-time PCR was conducted by a method similar to that in Example 1 except that the aforementioned combinations of primers and a probe were used and that the prepared plasmid mixtures were used as template DNA.

(Result)

Table 6 illustrated the measurements (pg/µL) of the plasmid in which the 16S rRNA gene derived from the bacterium of the genus *Nitrobacter* was introduced, with the plasmid quantified by real-time PCR. If the combinations 1-2, 1-4, 1-5, 1-7, 1-9 and 1-10 of primers and a probe with the primers designed within V6-V7 regions were used, it was possible to specifically detect only the plasmid derived from the genus *Nitrobacter* and to quantify the plasmid at concentrations down to 0.001 pg/µL, even when plasmids in which the 16S rRNA genes derived from a plurality of kinds of bacteria were introduced as template DNA. At this time, the plasmids in which the 16S rRNA gene derived from a bacterium other than the bacteria of the genus *Nitrobacter* was introduced were below the detection limit (0.001 pg/µL). Meanwhile, if the combination 2-5 of primers and a probe with the primers designed within the V5-V7 regions was used, it was possible to specifically detect only the plasmid derived from the genus *Nitrobacter* at concentrations down to 1 pg/µL, but it was not possible to detect and quantify the plasmid derived from the genus *Nitrobacter* at concentrations of 0.1 pg/µL or less.

TABLE 6

| | | | Theoretical values of plasmid (pg/µL) | | | |
|---|---|---|---|---|---|---|
| | | | 1 | 0.1 | 0.01 | 0.001 |
| Measurements of plasmid (pg/µL) | Combinations | 1-2 | 3.3 | 0.081 | 0.0085 | 0.00017 |
| | | 1-4 | 2.2 | 0.11 | 0.011 | 0.0010 |
| | | 1-5 | 2.5 | 0.10 | 0.013 | 0.00085 |
| | | 1-7 | 2.9 | 0.053 | 0.0057 | 0.00085 |
| | | 1-9 | 1.7 | 0.082 | 0.011 | 0.00047 |
| | | 1-10 | 2.1 | 0.056 | 0.0064 | 0.00069 |
| | | 2-5 | 1.4 | Below detection limit | Below detection limit | Below detection limit |

Example 4: Specificity Test with 1 Kind of Genomic DNA (Materials)

The combination 1-9 of primers and a probe

Genomic DNAs derived from various kinds of bacteria (derived from the bacteria set forth in Table 7)

(Method)

Real-time PCR was conducted by a method similar to that in Example 1 except that the combination 1-9 of primers and a probe was used and that genomic DNAs (1 ng/µL) derived from the bacteria set forth in Table 7 were used as template DNA.

Table 7 illustrates the bacteria from which the genomic DNAs used in the test were derived and the results of detection of their genomic DNAs. Using the combination 1-9 of primers and a probe, it was possible to detect genomic DNA of *Nitrobacter winogradskyi* NBRC14297, a bacterium of the genus *Nitrobacter*, at concentrations down to 0.001 ng/µL. Meanwhile, genomic DNAs derived from the other bacteria were below the detection limit (0.001 ng/µL). Therefore, it was demonstrated that it is possible to specifically detect the bacteria of the genus *Nitrobacter* with this combination of primers and probe even when genomic DNA is used.

TABLE 7

| Bacterium from which genomic DNA is derived | Theoretical value of genomic DNA (ng/µL) | Detection result of genomic DNA |
|---|---|---|
| *Bacillus licheniformis* IFO 12200t | 1 | Below detection limit |
| *Bacillus subtilis* JCM 1465t | 1 | Below detection limit |
| *Rhizobium galegae* IFO 14965t | 1 | Below detection limit |
| *Rhizobium meliloti* IFO 14782t | 1 | Below detection limit |
| *Rhizobium leguminosarum* IFO 14778t | 1 | Below detection limit |
| *Escherichia coli* JM109 | 1 | Below detection limit |
| *Rhodococcus rhodochrous* JCM 3202t | 1 | Below detection limit |
| *Sphingomonas parapaucimobilis* JCM 7510t | 1 | Below detection limit |
| *Sphingomonas paucimobilis* IFO 13935t | 1 | Below detection limit |
| *Sphingomonas yanoikuyae* JCM 7371t | 1 | Below detection limit |
| *Sphingomonas adhaesiva* JCM 7370t | 1 | Below detection limit |
| *Bradyrhizobium diazoefficiens* NBRC14792 | 1 | Below detection limit |
| *Bradyrhizobium japonicum* NBRC14783 | 1 | Below detection limit |
| *Nitrobacter winogradskyi* NBRC14297 | 1 | Detectable |
| | 0.1 | Detectable |
| | 0.01 | Detectable |
| | 0.001 | Detectable |

Example 5: Quantifiability Test with Mixed Genomic DNAs of Plurality of Kinds (Materials)

The combination 1-9 of primers and a probe

Genomic DNA derived from *Nitrobacter winogradskyi* NBRC4297

Genomic DNAs derived from various kinds of bacteria (derived from the bacteria set forth in Table 8)

(Method)

To a mixture (the final concentrations of the various kinds of genomic DNAs were each 100 pg/μL) in which genomic DNAs derived from the bacteria set forth in Table 8 were mixed, genomic DNA derived from *Nitrobacter winogradskyi* NBRC14297 was admixed at a final concentration of 100 pg/μL, 10 pg/μL, 1 pg/μL or 0.1 pg/μL to prepare a genomic DNA mixture. Real-time PCR was conducted by a method similar to that in Example 1 except that the combination 1-9 of primers and a probe was used and that the prepared genomic DNA mixtures were used as template DNA.

TABLE 8

| Name of bacterium | Genomic DNA concentration (pg/μL) |
|---|---|
| *Bacillus licheniformis* IFO 12200t | 100 |
| *Bacillus subtilis* JCM 1465t | 100 |
| *Rhizobium galegae* IFO 14965t | 100 |
| *Escherichia coli* JM109 | 100 |
| *Rhodococcus rhodochrous* JCM 3202t | 100 |
| *Sphingomonas parapaucimobilis* JCM 7510t | 100 |
| *Sphingomonas paucimobilis* IFO 13935t | 100 |
| *Sphingomonas yanoikuyae* JCM 7371t | 100 |
| *Sphingomonas adhaesiva* JCM 7370t | 100 |

(Result)

Table 9 illustrates the results of quantification of genomic DNA derived from *Nitrobacter winogradskyi* NBRC14297 with the combination 1-9 of primers and a probe. The measurements of genomic DNAs illustrated in Table 9 are the means of results of measurements of 3 samples. If the combination 1-9 of primers and a probe was used, then it was possible to specifically detect only the genomic DNA derived from *Nitrobacter winogradskyi* NBRC14297 and to quantify the concentrations down to 0.1 pg/μL even when genomic DNAs derived from a plurality of kinds of bacteria as template DNA. At this time, the genomic DNAs derived from the other kinds of bacteria were below the detection limit (0.1 pg/μL).

TABLE 9

| Theoretical value of genomic DNA (pg/μL) | 100 | 10 | 1 | 0.1 |
|---|---|---|---|---|
| Measurement of genomic DNA (pg/μL) | 71 | 12 | 1.7 | 0.27 |

Example 6: Detection and Quantification of Bacteria of Genus *Nitrobacter* with Activated Sludge (Materials)

The combination 1-9 of primers and a probe

Genomic DNAs derived from activated sludge samples 1-11 (amount of activated sludge sampled was 1.5 mL and amount of elution was 150 μL).

(Method)

Real-time PCR was conducted by a method similar to that in Example 1 except that the combination 1-9 of primers and a probe was used and that genomic DNAs (2 μL) derived from the activated sludge samples 1-11 were used as template DNA.

(Result)

Table 10 illustrates the result of quantification of the genomic DNAs derived from the activated sludge samples 1-11 in terms of the plasmid concentration when the combination 1-9 of primers and a probe was used. It was demonstrated from this result that using the combination 1-9 of primers and a probe, the bacteria of the genus *Nitrobacter* can be directly detected from genomic DNA derived from activated sludge.

TABLE 10

| Sample name | Measurement (pg/μL) |
|---|---|
| Activated sludge sample 1 | 0.089 |
| Activated sludge sample 2 | 0.088 |
| Activated sludge sample 3 | 0.071 |
| Activated sludge sample 4 | 0.056 |
| Activated sludge sample 5 | 0.073 |
| Activated sludge sample 6 | 0.064 |
| Activated sludge sample 7 | 0.061 |
| Activated sludge sample 8 | 0.100 |
| Activated sludge sample 9 | 0.044 |
| Activated sludge sample 10 | 0.038 |
| Activated sludge sample 11 | 0.036 |

From these results, it was possible to specifically detect and accurately quantify the bacteria of the genus *Nitrobacter* by using primers and a probe designed within the V6-V7 regions even in systems in which a plurality of bacterial kinds is present.

The invention claimed is:

1. A method for detecting a bacterium of the genus *Nitrobacter* in activated sludge, comprising:
   a) obtaining DNA prepared from activated sludge; and
   b) detecting whether a bacterium of the genus *Nitrobacter* is present in the activated sludge sample by:
      a first step of amplifying a nucleotide using the DNA prepared from activated sludge as a template and primers capable of amplifying a nucleotide sequence of consecutive 110 nucleotides or more and 157 nucleotides or less in the nucleotide sequence of SEQ ID NO:1 to obtain an amplified product; and
      a second step of detecting the amplified product;
      wherein the primers used in the first step are a first primer and a second primer, wherein the first primer consists of the nucleotide sequence selected from the group consisting of SEQ ID NO:4 to SEQ ID NO:8 and the second primer consists of the nucleotide sequence selected from the group consisting of SEQ ID NO:9 or SEQ ID NO:10, and
   wherein the second step comprises detecting the amplified product using a probe comprising the nucleotide sequence of SEQ ID NO:11, wherein the probe is modified with a fluorescent substance.

2. The method according to claim 1, wherein the first primer consists of the nucleotide sequence of SEQ ID NO:7 and the second primer consists of the nucleotide sequence.

* * * * *